United States Patent [19]
Suzuki et al.

[11] 4,307,036
[45] Dec. 22, 1981

[54] METHOD FOR PREPARING A MIXTURE OF STEREOISOMERS OF α-CYANO-3-PHENOXYBENZYL 2-(4-SUBSTITUTED-PHENYL)ISOVALERATES

[75] Inventors: Yukio Suzuki; Kohichi Aketa, both of Toyonaka; Masachika Hirano, Ibaraki, all of Japan

[73] Assignee: Sumitomo Chemical Company, Limited, Osaka, Japan

[21] Appl. No.: 139,526

[22] Filed: Apr. 11, 1980

Related U.S. Application Data

[63] Continuation-in-part of Ser. No. 7,536, Jan. 29, 1979, Pat. No. 4,238,406.

[30] Foreign Application Priority Data

Jan. 27, 1978 [JP] Japan ................................. 53-8621

[51] Int. Cl.³ ........................................... C07C 121/75
[52] U.S. Cl. ................................. 260/465 D; 424/304
[58] Field of Search ................................. 260/465 D

[56] References Cited

U.S. PATENT DOCUMENTS 4,176,195  11/1979  Stoutamire ........................... 424/304

FOREIGN PATENT DOCUMENTS 2001964A  2/1979  United Kingdom .

Primary Examiner—Dolph H. Torrence
Attorney, Agent, or Firm—Sughrue, Mion, Zinn, Macpeak & Seas

[57] ABSTRACT

A method for preparing α-cyano-3-phenoxybenzyl 2-(4-substituted-phenyl)isovalerates which consist substantially of or are rich in the enantiomer pair (S)-α-cyano-3-phenoxybenzyl (S)-2-(4-substituted-phenyl)isovalerate and (R)-α-cyano-3-phenoxybenzyl (R)-2-(4-substituted-phenyl)isovalerate.

46 Claims, No Drawings

METHOD FOR PREPARING A MIXTURE OF STEREOISOMERS OF α-CYANO-3-PHENOXYBENZYL 2-(4-SUBSTITUTED-PHENYL)ISOVALERATES

RELATED APPLICATIONS

This application is a continuation in part of Ser. No. 7,536, filed Jan. 29, 1979, U.S. Pat. No. 4,238,406.

BACKGROUND OF THE INVENTION

1. Field of the Invention

This invention relates to α-cyano-3-phenoxybenzyl 2-(4-substituted-phenyl)isovalerates having a high insecticidal and acaricidal activity and a process for preparing the same. More particularly, the present invention relates to α-cyano-3-phenoxybenzyl 2-(4-substituted-phenyl)-isovalerates which consist substantially of or are rich in the enantiomer pair (S)-α-cyano-3-phenoxybenzyl (S)-2-(4-substituted-phenyl)isovalerate and (R)-α-cyano-3-phenoxybenzyl (R)-2-(4-substituted-phenyl)isovalerate.

The compounds to which the invention is directed are α-cyano-3-phenoxybenzyl 2-(4-substituted-phenyl)isovalerates of the formula (I):

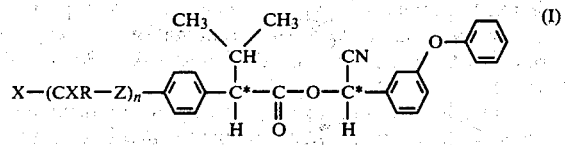

wherein X is hydrogen, Cl or F; R is Cl, F, hydrogen, lower alkyl or lower haloalkyl; Z is oxygen or sulfur; and n is 0 or 1, with the proviso that when n is 0, then X is not hydrogen. These compounds have a low toxicity to mammals and a broad range of insecticidal and acaricidal activity. For example, the compound fenvalerate wherein X is Cl and n is 0 is disclosed in Japanese Patent Application (OPI) No. 26425/74 (the term "OPI" as used herein refers to a "published unexamined Japanese patent application"), and U.S. Pat. No. 3,996,244. The compound wherein X is F; R is H, Z is O and n is 1 (difluoromethoxy) is disclosed in British Pat. No. 2017688A published Oct. 10, 1979.

The invention is particularly directed to compounds of the formula (II):

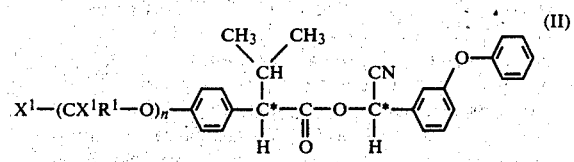

wherein $X^1$ is Cl or F; $R^1$ is hydrogen, methyl or methyl substituted with F; and n is 0 or 1, with the proviso that when n is 1, $X^1$ is F.

Each compound of formulas (I) and (II) contains two asymmetric carbon atoms in the molecule (designated by an asterisk (*) in the formula) and, therefore, includes four optical isomers.

In this specification, α-cyano-3-phenoxybenzyl 2-(4-substituted-phenyl)isovalerate and its isomers will be identified as follows: α-cyano-3-phenoxybenzyl 2-(4-substituted-phenyl)isovalerate of the formulas (I) and (II) above will be referred to hereinafter as "substituted phenylisovalerate", or "S phenylisovalerate"; (R, S)-α-cyano-3-phenoxybenzyl (S)-2-(4-substituted-phenyl)isovalerate will be referred to as "S phenylisovalerate A"; (S)-α-cyano-3-phenoxybenzyl (S)-2-(4-substituted-phenyl)isovalerate will be referred to as "S phenylisovalerate Aα"; (R)-α-cyano-3-phenoxybenzyl (S)-2-(4-substituted-phenyl)isovalerate will be referred to as "S phenylisovalerate Aβ"; (S)-α-cyano-3-phenoxybenzyl (R)-2-(4-substituted-phenyl)isovalerate will be referred to as "S phenylisovalerate Bα", (R)-α-cyano-3-phenoxybenzyl (R)-2(4-substituted-phenyl)isovalerate will be referred to as "S phenylisovalerate Bβ"; the enantiomer pair consisting of a mixture of S phenylisovalerate Aβ and S phenylisovalerate Bα will be referred to as "S phenylisovalerate X"; and the enantiomer pair consisting of a mixture of S phenylisovalerate Aα and S phenylisovalerate Bβ will be referred to as "S phenylisovalerate Y". Y-rich and X-rich S phenylisovalerates will be used to designate S phenylisovalerate mixtures rich in S phenylisovalerate Y and S phenylisovalerate X, respectively. In the case where the 4-substituent on the phenyl group is chloro, to designate the specific compound the term fenvalerate will be used instead of S phenylisovalerate.

The relationship between the absolute configurations of the asymmetric carbon atoms in the acid moiety and alcohol moiety to the insecticidal and acaricidal activity of the compounds has already been reported. The following references describe fenvalerate Aα, having (S)-configurations at the asymmetric carbon atoms on both acid and alcohol moieties, as the most active stereoisomer of the four. Japanese Patent Application (OPI) No. 24019/78 (corresponding to U.S. Ser. No. 825,570, filed Aug. 17, 1977); Japanese Patent Application (OPI) No. 59646/78; Ohno et al., *J. Pesticide Science*, 2 (Special Issue), December 1977; and Aketa et al., *Agr. Bio. Chem*. 42, 895 (1978). The British Patent Application No. 2017688A shows that the isomers of S phenylisovalerate wherein the phenyl substituent is difluoromethoxy having (S)-configuration at the acid asymmetric carbon atom and being racemic at the corresponding alcohol carbon are more active than the full racemate. U.S. Pat. No. 4,176,195 discloses fenvalerate Y as a highly active pesticide.

In the case of esters of α-cyano-3-phenoxybenzyl alcohol and a dihalovinylcyclopropanecarboxylic acid, for example, cypermethrin (NRDC-149), i.e., α-cyano-3-phenoxybenzyl 2,2-dimethyl-3-(2,2-dichlorovinyl)cyclopropanecarboxylate, and α-cyano-3-phenoxybenzyl 2,2-dimethyl-3-(2,2-dibromovinyl)cyclopropanecarboxylate, the (S)-isomers of the alcohol moiety in the esters are more active than the (R)-isomers thereof. Racemization (or epimerization) of α-cyano-3-phenoxybenzyl esters of d-cis-2,2-dimethyl-3-(2,2-dibromovinyl)cyclopropanecarboxylic acid and d-cis-2,2-dimethyl-3-(2,2-dichlorovinyl)cyclopropanecarboxylic acid in the presence of a basic catalyst has been reported and, furthermore, (S)-isomer esters of the alcohol moieties have been obtained from the ester having (R,S)-alcohol and d-cis isomer of these dihalovinylcyclopropanecarboxylic acids as described in Belgian Pat. No. 853,866 (and Belgian Pat. No. 853,867 (1977)).

Although these patents claim the "chiral acid" ester, in the examples, only cases of d-cis-dihalovinylcyclopropanecarboxylic acid esters are shown. Particularly, in the latter case, the patent requires that one stereoisomer of a diastereomer pair must crystallize selectively from the solution of the mixture with the other diastereoisomer of the pair; therefore every "chiral acid" ester stereoisomer cannot be obtained.

In the case of fenvalerate, the epimerization of the alcohol moiety of the optically active fenvalerate and processes for obtaining fenvalerate Aα fenvalerate A by a selective crystallization or crystallization combined with concurrent epimerization have been applied for in U.S. Application Ser. No. 922,476, filed July 7, 1978 (corresponding British Patent Specification No. 2001964A, published Feb. 14, 1979. However, in these methods for obtaining fenvalerates, optical resolution of the carboxylic acid is necessary in the synthesis of fenvalerate A; for example, these resolution methods involve reaction with an optically active base, selective crystallization of the resulting diastereomer salt, purification of the salt and decomposition of the salt to obtain the optically active carboxylic acid. Furthermore, for economy the enantiomeric acid by-product must be reused, for example, after racemization. On the other hand, the racemization of the useful optically active acid or derivatives thereof must be avoided and, as a result, the reaction conditions are limited.

SUMMARY OF THE INVENTION

This invention provides a process for preparing a stereoisomer mixture of S phenylisovalerate, i.e., "S phenylisovalerate Y" or Y-rich S phenylisovalerate. S Phenylisovalerate Y's insecticidal and acaricidal activities are higher than those of S phenylisovalerates which are prepared by common procedures using optically inactive starting materials such as racemic S phenylisovalerate.

An insecticidal composition comprising S phenylisovalerate Y or Y-rich S phenylisovalerate as an active ingredient possesses an unexpectedly high insecticidal and acaricidal activity, and it can be used practically.

DETAILED DESCRIPTION OF THE INVENTION

The present invention is directed to compounds and isomers of compounds of the formula (I):

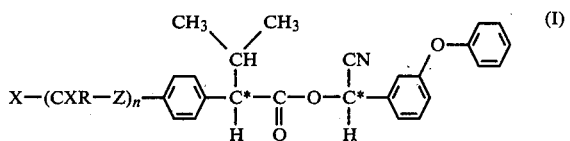

wherein X is hydrogen, Cl or F; R is Cl, F, hydrogen, lower alkyl or lower haloalkyl; Z is oxygen or sulfur and n is 0 or 1, with the proviso that when n is 0, then X is not hydrogen. Suitable examples of halogens for the lower haloalkyl are Cl and F. The term "lower" for the lower alkyl and lower haloalkyl referred to herein means the carbon number of 1 or 2.

The invention is particularly directed to compounds of the formula (II):

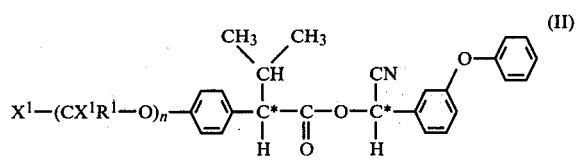

wherein $X^1$ is Cl or F; $R^1$ is hydrogen, methyl or methyl substituted with F; and n is 0 or 1, with the proviso that when n is 1, $X^1$ is F.

Exemplary of compounds of formulas (I) and (II) are the following:

α-Cyano-3-phenoxybenzyl 2-(4-chlorophenyl)isovalerate
α-Cyano-3-phenoxybenzyl 2-(4-methoxyphenyl)isovalerate
α-Cyano-3-phenoxybenzyl 2-(4-difluoromethoxyphenyl)isovalerate
α-Cyano-3-phenoxybenzyl 2-(4-trifluoromethoxyphenyl)isovalerate
α-Cyano-3-phenoxybenzyl 2-(4-ethoxyphenyl)isovalerate
α-Cyano-3-phenoxybenzyl 2-[4-(2,2-dichloroethoxy)phenyl]isovalerate
α-Cyano-3-phenoxybenzyl 2-[4-(2,2-difluoroethoxy)phenyl]isovalerate
α-Cyano-3-phenoxybenzyl 2-(4-difluoromethylthiophenyl)isovalerate
α-Cyano-3-phenoxybenzyl 2-(4-fluorophenyl)isovalerate
α-Cyano-3-phenoxybenzyl 2-[4-(1,1,2,2-tetrafluorothoxy)phenyl]isovalerate As defined above, these various compounds are referred to herein as S phenylisovalerates and, in particular, the various isomers and combinations thereof are referred to as S phenylisovalerate Aα, Aβ, Bα, Bβ, X and Y.

This invention provides a process for preparing an S phenylisovalerate Y which comprises precipitating the crystals of S phenylisovalerate Y from an S phenylisovalerate solution in the presence or absence of a basic catalyst; or for preparing a Y-rich S phenylisovalerate which comprises precipitating crystals of S phenylisovalerate Y in the presence of a basic catalyst and then concentrating the resulting crystal-containing slurry as it is or after removal or deactivation of the catalyst.

The present invention provides a method for precipitating S phenylisovalerate Y as crystals from S phenylisovalerate without a catalyst (referred to as "method A" hereinafter). In another case, an S phenylisovalerate X-rich mother liquor, which has been separated from the S phenylisovalerate Y crystals, is brought into contact with a basic catalyst, thereby epimerizing the alcohol moiety until the ratio of S phenylisovalerate X to S phenylisovalerate Y reaches equilibrium, and then the crystallization operation is carried out again. Thus, S phenylisovalerate can finally be converted to S phenylisovalerate Y almost quantitatively (hereafter referred to as "method A'"). By the methods A and/or A', S phenylisovalerate containing practically no S phenylisovalerate X can be obtained.

In method A, as starting material S phenylisovalerate, one can use Y-rich S phenylisovalerate. Preferably, for example, S phenylisovalerate containing more than 60% by weight S phenylisovalerate Y can be used as the starting material and can be prepared, for example, by method C described below. In method A, S phenylisovalerate Y can be prepared in a good yield corresponding to the S phenylisovalerate Y content of the S phenylisovalerate starting material.

Further, in the crystallization of S phenylisovalerate Y according to method A, the present invention also provides a method which comprises carrying out the crystallization in the presence of a basic catalyst (referred to as "method B" hereinafter). The basic catalyst acts to epimerize the asymmetric carbon atom in the alcohol moiety. By adding this catalyst to the crystallization system of S phenylisovalerate Y, it becomes possible to prepare S phenylisovalerate Y crystals in amounts larger than that initially contained in the S phenylisovalerate. The reason for this is considered as follows: The ratio of S phenylisovalerate Y to S phenylisovalerate X in the mother liquid decreases to less than that in the initial state by crystallization of S phenylisovalerate Y, and the decrease of S phenylisovalerate Y is compensated for by epimerization of S phenylisovalerate X to S phenylisovalerate Y in the mother liquor. As a result, whereas method A theoretically produces S phenylisovalerate Y crystals in an amount of 50 parts, generally only 20 to 30 parts, upon crystallization from 100 parts of starting S phenylisovalerate, method B produces 40 to 80 parts or more of S phenylisovalerate Y crystals from 100 parts of starting S phenylisovalerate.

Further, the present invention provides a method for preparing a Y-rich S phenylisovalerate mixture which comprises concentrating the mother liquor together with S phenylisovalerate Y obtained by method B (referred to as "method C" hereinafter). In method B, the S phenylisovalerate in the mother liquor separated from the S phenylisovalerate Y crystals by filtration or the like contains about half S phenylisovalerate Y. If S phenylisovalerate in the mother liquor recovered in method B is reused as a starting material for method B, loss in amount becomes small, but this method is not practical considering that the impurities are increasingly concentrated.

Method C recovers the S phenylisovalerate of the mother liquor together with S phenylisovalerate Y crystals thereby making effective use of S phenylisovalerate Y contained in the mother liquor. Simple concentration after crystallization is easy but the catalyst remains, and, therefore, attention should be given to the danger that the S phenylisovalerate Y is isomerized into S phenylisovalerate by epimerization by the action of the remaining catalyst. This danger can be avoided by deactivating the catalyst with addition of an acidic substance prior to concentration, but the catalyst components still remain in the product. When the catalyst or its deactivated product is insoluble, it can be removed by filtration and the like. When it is water-soluble, it can be conveniently removed by washing it with water as it is when the solvent is water-insoluble, or by adding a water-insoluble solvent followed by washing with water when the solvent is water-soluble. Alternatively, it may be possible to precipitate S phenylisovalerate Y as crystals and then to use the resulting slurry for preparation as it is or after more deactivation of the catalyst.

According to method C, as described above, it is possible to convert racemic S phenylisovalerate originally comprising 45 to 50 parts of S phenylisovalerate Y and 55 to 50 parts of S phenylisovalerate X into Y-rich S phenylisovalerate almost quantitatively.

In accordance with the present invention it has been found that S phenylisovalerate Y crystallizes and can be selectively crystallized from the S phenylisovalerate solution. As shown in the following examples, this crystallization from the solution of S phenylisovalerate proceeds slowly. Fenvalerate Y had never been refined previously. Y-rich fenvalerate, in which the fenvalerate Y content is below 90%, has almost the same physical properties as fenvalerate prepared in common procedures and had never been crystallized previously.

S phenylisovalerate Y or Y-rich S phenylisovalerate may be racemic or optically active. The starting material need not be optically active and is usually an essentially racemic mixture consisting of 45 to 55 parts of S phenylisovalerate Y.

As is the case with other pyrethroid-type esters, the crystallization of the above compounds is not apparent and cannot be realized from the properties of racemic S phenylisovalerate. Fenvalerate itself is a viscous oily substance. For example, with respect to α-cyano-3-phenoxybenzyl 2,2-dimethyl-3-(2,2-dichlorovinyl)cyclopropanecarboxylate, which is a pyrethroid-type ester having the same alcohol moiety as the above compound, no ester thereof having a d-trans (1R, 3S) acid moiety and an (S), (R) or racemic alcohol moiety has been known to crystallize. However, both a 1:1 (by weight) mixture (m.p. 75.0°–76.8° C.) of an ester having a d-trans acid moiety and an (R) alcohol moiety and an ester having an l-trans (1S, 3R) acid moiety and an (S) alcohol moiety and a 1:1 (by weight) mixture (m.p. 78.5°–80° C.) of an ester having a d-trans acid moiety and an (S) alcohol moiety and an ester having an l-trans acid moiety and an (R) alcohol moiety have been obtained as crystals.

It has also been found that in α-ethynyl-3-phenoxybenzyl 2-(4-chlorophenyl)isovalerate, which is a pyrethroid-type ester having a very similar chemical structure to fenvalerate, a mixture (m.p. 46°–47° C.) of esters having a racemic acid moiety and a racemic alcohol moiety, a mixture of two diastereomers thereof (each being racemic), and an ester thereof having an optically active acid moiety are crystalline at room temperature. When the ester mixture having a racemic acid moiety and a racemic alcohol moiety is recrystallized from hexane, a diastereomer having a melting point of 87° to 88° C. and a very weak insecticidal activity crystallizes predominately. The ester recovered from the mother liquor is a diastereomer (m.p. 51°–52° C.) having a higher insecticidal activity. On the other hand, when the ester having an optically active acid moiety (m.p. 61°–62° C.) is subjected to this procedure, selective crystallization of a diastereomer is not observed, and no single stereoisomer is crystallized.

In allethrin (i.e., allethronyl chrysanthemate) a well known synthetic pyrethroid-type ester which includes four diastereomers, only a diastereomer ("crystalline allethrin") consisting of an ester having a d-trans acid moiety and an l-alcohol moiety and an ester having an l-trans acid moiety and a d-alcohol moiety is known to crystallize (e.g., as disclosed in M. Matsui and I. Yamamoto,

*Natural Occurring Insecticides*, M. Jacobson, D. G. Grosby Eds., pp. 38–42, Marcel Dekker, Inc., New York (1971). No enantiomer of "crystalline allethrin" is known to crystallize by itself.

These facts show that it is very difficult to predict which optical isomers or mixtures thereof can be obtained as crystals, and that even when a certain optical isomer is obtained as a crystal, it is difficult to predict whether that optical isomer can be selectively crystallized from a mixture of that optical isomer with other optical isomers.

Fenvalerate Y is a mixture which comprises fenvalerate Aα and fenvalerate Bβ, and the melting point is lower than that of fenvalerate Aα. Furthermore, the solubilities of fenvalerate Y are greater than those of fenvalerate Aα. Therefore, the crystallization condition of fenvalerate Y is more restricted than that for fenvalerate Aα.

In the methods of the present invention, it is not always necessary that the acid moiety or alcohol moiety of the starting S phenylisovalerate form a racemate, and the Y-rich S phenylisovalerate Y produced is not necessarily a racemate. In the methods B and C of the present invention, there is of course no limitation on the weight ratio of S phenylisovalerate X to S phenylisovalerate Y in the starting S phenylisovalerate. In method A, Y-rich S phenylisovalerate can be used to obtain S phenylisovalerate Y.

In carrying out the present invention, a solvent is generally used since the S phenylisovalerates generally are liquids having little or no fluidity at crystallization temperature. The solvent is not particularly limited if the starting S phenylisovalerate and S phenylisovalerate X are suitably soluble in it but product S phenylisovalerate Y is hardly soluble in it. As the solvent, there may be given, for example, hydrocarbon solvents (e.g., hexane, heptane, methylcyclohexane, etc.) and lower alcohols (e.g., methanol, ethanol, etc.). Lower alcohols are preferred, and of the lower alcohols, methanol is particularly preferred. Other preferred solvents are the mixture of a lower alcohol, preferably methanol, and an aliphatic or alicyclic hydrocarbon, such as hexane, heptane or methylcyclohexane. Other solvents such as aromatic hydrocarbons (e.g., benzene, toluene, monochlorobenzene, xylene, etc.) can be used in admixture with the alicyclic or aliphatic hydrocarbon but not in amounts larger than the aliphatic or alicyclic hydrocarbon. The concentration of S phenylisovalerate is optionally selected within the range of 1 to 95% by weight, but concentrations of 20 to 80% by weight are preferred.

For the purpose of crystallization, it is desirable to add seed crystals. Preferred seed crystals are the crystals of S phenylisovalerate Y, but the crystal of S phenylisovalerate Aα or S phenylisovalerate Bβ, or a mixture of both crystals in optional proportions may also be used satisfactorily. The amount of seed crystal is not particularly limited, but the crystallization or reaction is faster with a larger amount of seed crystals, preferably an amount greater than 5% based on the S phenylisovalerate in the solution. Therefore, in the method B or C, it is better to perform the step of crystallization with epimerization continuously or semi-continuously.

In the method A', epimerization of the S phenylisovalerate X-rich fenvalerate in the mother liquor separated from S phenylisovalerate Y crystals, can be achieved by contacting the S phenylisovalerate solution with a basic catalyst. Any solvent may be used for this reaction which does not decompose or form impurities by reaction with the S phenylisovalerate or catalyst, if it can dissolve S phenylisovalerate. Suitable solvents include, for example, methanol, ethanol, ethyl acetate, toluene, hexane, chloroform, acetonitrile, diethyl ether and the like.

The catalyst may be optionally selected from basic substances such as nitrogen-containing bases, phosphorus-containing bases, metal oxides, metal hydroxides, salts of metals with weak acids such as carbonic acid, silicic acid or hydrocyanic acid, and base-type ion exchange resins. Specific examples of catalysts which can be used include ammonia; aliphatic amines such as methylamine, ethylamine, n-propylamine, isopropylamine, n-butylamine, n-pentylamine, diethylamine, di-n-propylamine, di-n-butylamine, triethylamine, tri-n-propylamine, tri-n-butylamine, cyclohexylamine, and ethanolamine; aromatic amines such as aniline, 1-naphthylamine and 2-naphthylamine; quaternary ammonium salts such as tetramethyl ammonium hydroxide and tetra-n-propyl ammonium hydroxide; nitrogen-containing heterocyclic compounds such as pyridine; quinoline, pyrrolidine and piperidine; phosphorus-containing bases such as triphenyl phosphine and tri-n-butyl phosphine; metal oxides such as calcium oxide, magnesium oxide, beryllium oxide, zinc oxide, silicon dioxide and alumina; metal hydroxides such as sodium hydroxide, potassium hydroxide, magnesium hydroxide and calcium hydroxide; weak acid metal salts such as sodium carbonate, potassium carbonate, barium carbonate and potassium cyanide; talc; bentonite; the bases described above adsorbed on silica gel, alumina or activated carbon; and base-type ion exchange resins which have a basic group such as an amino group or a quaternary ammonium group. Suitable commercially available base-type ion exchange resins which can be used include "DOWEX 2×8" (a trademark for a product of the Dow Chemical Company, which is a strong base-type ion exchange resin made from a styrene-divinylbenzene copolymer having a quaternary ammonium group ($-NR_3^+ +OH^-$) incorporated therein), "AMBERLITE IR-45" (a trademark for a product of the Rohm & Haas Company, which is a weak base-type anion exchange resin having $-N(R)_2$, $-NH(R)$ and $-NH$ moieties as exchanging moieties), "AMBERLITE IRA-93" (a trademark for a product of the Rohm & Haas Company, which is a weak base-type anion exchange resin (MR-type) having an $-N(CH_3)_2$ moiety as an exchanging moiety), "AMBERLIST A-21" (a trademark for a product of the Rohm & Haas Company, which is a weak base-type anion exchange resin (MR-type) having an $-N(CH_3)_2$ moiety as an exchanging moiety and which is useful for non-aqueous solution), and "AMBERLIST A-27" (a trademark for a product of the Rohm & Haas Company, which is a strong base-type anion exchange resin (OH-type) having an

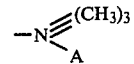

moiety as an exchanging moiety and which is useful for non-aqueous solutions).

From the standpoint of ease of removal of the catalyst after the epimerization reaction, those basic substances which are substantially insoluble in the solvents described above, especially base-type ion exchange resins, are preferred. It is to be understood that the basic catalyst is not limited to the materials exemplified hereinabove, and other substances can also be selected without departing from the spirit and scope of the invention.

In the method A', the catalyst may be added to the solution containing the X-rich S phenylisovalerate to be epimerized, or the solution containing the X-rich S phenylisovalerate may be passed through a column packed with the catalyst.

Suitable temperatures at which the epimerization can be accomplished are those at which the ester does not undergo any significant decomposition. The rate of epimerization is higher at higher temperatures. Preferably, the epimerization temperature ranges from about $-50°$ C. to the boiling point of the solvent, more preferably from $-20°$ C. to 150° C.

After epimerization is finished, removal of the catalyst and concentration of the solution are carried out, if necessary, and then the same crystallization as in the method A can be applied. The epimerization is carried out most easily, if the solvent is common to epimerization and crystallization.

As the basic catalyst used in the methods B and C there are nitrogen bases, phosphorus bases, quaternary ammonium hydroxides, metal-containing bases such as hydroxides, oxides, alcoholates, hydrides, carbonates, cyanides or amides of alkali metals (e.g., sodium, potassium, etc.) or alkaline earth metals (e.g., calcium, etc.), and basic ion-exchange resins. Of these basic catalysts, those which are soluble in the S phenylisovalerate solution are preferred, and nitrogen bases such as ammonia and triethylamine are particularly preferred.

The amount of the basic catalyst based on S phenylisovalerate is optionally selected within the range of 0.001 to 100 mol%. For weak bases such as nitrogen bases and phosphorus bases the range is preferably 1 to 100 mol%, while the amount is preferably 10 mol% or less for strong bases such as a quaternary ammonium hydroxide, sodium hydroxide, potassium hydroxide, sodium methylate and sodium hydride since decomposition takes place voluntarily.

In the present invention, crystallization temperatures lower than the melting point of the S phenylisovalerate Y are theoretically suitable, but preferably the temperature is 10° to −50° C., particularly −5° C. to −35° C.

In the method B or C, the basic catalyst must be removed from the S phenylisovalerate Y or Y-rich S phenylisovalerate obtained or neutralized. Otherwise, the ratio of S phenylisovalerate X to S phenylisovalerate Y can revert to about 50:50.

As is apparent from the aforesaid explanation, S phenylisovalerate Y itself or Y-rich S phenylisovalerate can be obtained from the commercially avaialable racemic S phenylisovalerate very simply and easily by the method of the present invention without applying troublesome methods such as optical resolution. Thus, the insecticidal and acaricidal activity of S phenylisovalerate can be increased and, therefore, the method of the present invention is economically very important.

In practical application S phenylisovalerate Y or Y-rich S phenylisovalerate may be used alone or in combination with a carrier for the convenience of use as a pesticide. The present compounds can be formulated into optional preparation forms without any special treating conditions according to the formulation of common pesticides. That is, the compounds may be formed into emulsifiable concentrates, wettable powders, dusts, granules fine granules, oil sprays, aerosols, heating fumigants (mosquito coils, electric mosquito killers, etc.), thermal fogging agents, non-heating fumigants and baits by methods well known to those skilled in the art, and they may be used in forms which are suitable for application and in combination with a carrier.

Furthermore, the insecticidal and acaricidal activity of the present compoounds can be increased by combination with known synergists for pyrethroids such as α-[2-(2-butoxyethoxy)ethoxy]-4,5-methylenedioxy-2-propyltoluene (hereinafter referred to as piperonyl butoxide), 1,2-methylenedioxy-4-[2-(octylsulfinyl)-propyl]benzene (hereinafter referred to as sulfoxide), 4-(3,4-methylenedioxyphenyl)-5-methyl-1,3-dioxane (hereinafter referred to as sufroxane), N-(2-ethylhexyl)-bicyclo[2,2,1]-hepta-5-ene-2,3-dicarboximide (hereinafter referred to as MGK-264), bis(2,3,3,3-tetrachloropropyl) ether (hereinafter referred to as S-421) and isobornylthiocyanoacetate (hereinafter referred to as Thanite); and with known synergists for allethrin or pyrethrins. For example, antioxidants or UV absorbers such as phenol derivatives including BHT and BHA, bisphenol derivatives, arylamine derivatives including phenyl-α-naphthylamine, phenyl-β-naphthylamine and condensation products of phenetidine and acetone, and benzophenone compounds.

Additionally, the present compounds can be formulated into multipurpose compositions having more superior activity in combination with other active ingredients such as allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as Chrysron (a registered trademark of Sumitomo Chemical Co., Ltd.)), 3-phenoxybenzyl chrysanthemate, 5-propargylfurfuryl chrysanthemate and 2-methyl-5-propargyl-3-furylmethyl chrysanthemate, including, for example, d-trans- and d-cis, trans-chrysanthemic acid esters thereof, pyrethrum extracts, d-trans- or d-cis, trans-chrysanthemic acid esters of d-allethrolone, 3-phenoxybenzyl 2,2-dimethyl-3-(2,2-dichlorovinyl)cyclopropanecarboxylate, α-cyano-3-phenoxybenzyl 2′,2′,3′,3′-tetramethylcyclopropanecarboxylate, other well known cyclopropanecarboxylic acid esters; organophosphorus type insecticides such as, for example, O,O-dimethyl-O-(3-methyl-4-nitrophenyl)phosphorothioate (hereinafter referred to as Sumithion (a registered trademark of Sumitomo Chemical Co., Ltd.)), O,O-dimethyl-O-4-cyanophenylphosphorothioate (hereinafter referred to as Cyanox (a registered trademark of Sumitomo Chemical Co., Ltd.)), O,O-dimethyl-O-(2,2-dichlorovinyl)-phosphate (hereinafter referred to as DDVO), O,O-dimethyl-O-4-methylmercapt-3-methylphenyl phosphorothioate, O,O-dimethyl-1-hydroxy-2,2,2-trichloroethyl phosphate, O,O-dimethyl-S-[1,2-bis(ethoxycarbonyl)ethyl]phosphorodithioate, 2-methoxy-4H-1,3,2-benzodioxaphospholin-2-sulfide, O,O-dimethyl-S-(1-ethoxycarbonyl-1-phenylmethyl)phosphorodithioate and O,O-diethyl-O-(2-isopropyl-4-methyl-6-pyrimidinyl)phosphorothioate; carbamate type insecticides such as, for example, 1-naphthyl-N-methylcarbamate, 3,4-dimethylphenyl-N-methylcarbamate (hereinafter referred to as Meobal (a registered trademark of Sumitomo Chemical Co., Ltd.)), 3-methylphenyl-N-methylcarbamate, 2-isopropoxyphenyl-N-methylcarbamate and S-methyl-N-[(methylcarbamoyl)oxy]thioacetimidate, N′-(2-methyl-4-chlorophenyl)-N,N-dimethylformamidine, 1,3-bis(carbamoylthio)-2-(N,N-dimethylamino)propane hydrochloride; other insecticides, acaricides, fungicides, nematocides, plant growth regulators, microbial insecticides such as B.T. and B.M., insect hormone compounds, herbicides, fertilizers or other agricultural chemicals. Furthermore, a synergistic effect owing to the combination can also be expected.

In the following Examples 1 to 14 and 19 to 24, the weight ratio of S phenylisovalerate X to S phenylisovalerate Y was measured by gaschromatographic analysis. The analysis conditions were as follows:

Column: 10% silicone DC-QF-1 (coated on Chromosorb AW-DMCS) 3 mm$\phi \times$3.0 m
Analysis temperature: 245° C.
Injection temperature: 250° C.
Nitrogen pressure: 2.0 kg/cm$^2$ In the analysis under the above conditions, the retention times of fenvalerate X and fenvalerate Y were about 38 minutes and 43 minutes, respectively.

Unless otherwise indicated in the following examples, S phenylisovalerate, S phenylisovalerate X and S phenylisovalerate Y refer to the racemates, and the weight ratio of S phenylisovalerate X to S phenylisovalerate Y is 50:50.

EXAMPLE 1

5 g of fenvalerate (purity: 98.0%) was dissolved in 2.5 g of methanol, and 5 mg of fenvalerate Y crystals were added thereto. The solution was allowed to stand for 83 days in a refrigerator (about 0° C.). The weight of crystals collected by filtration was 1.0 g (yield 20%). The ratio of fenvalerate X to fenvalerate Y in the crystals was 1.0:99.0.

EXAMPLE 2

25 g of fenvalerate (purity: 98.0%) was dissolved in 25 g of methanol, and 10 mg of fenvalerate Y crystals were added thereto. The solution was stirred at 6° C. for 20 days. The weight of the crystals collected by filtration was 4.9 g (yield 20%). The ratio of fenvalerate X to fenvalerate Y was 4:96.

The weight of fenvalerate recovered by concentrating the mother liquor was 20.0 g, and the ratio of fenvalerate X to fenvalerate Y in the recovered fenvalerate was 63:37.

EXAMPLE 3

15 g of the fenvalerate recovered from the mother liquor in Example 2 was dissolved in 75 g of methanol. This solution was passed downward over 5 hours through a glass column packed with 100 cc of a basic ion exchange resin (Amberlist A-21) slurried in methanol. Thereafter, 400 g of methanol was passed downward through the column over 3 hours. The eluates from the column were combined, and a part of the liquor was analyzed by gas chromatography. It was found that the ratio of fenvalerate X to fenvalerate Y was 53:47. The combined eluate was concentrated to a weight of 30 g under reduced pressure, and 10 mg of fenvalerate Y crystals were added thereto again. Crystallization was carried out at −6° C. for 20 days for stirring.

The weight of the crystals obtained was 2.3 g (yield 15%), and the ratio of fenvalerate X to fenvalerate Y was 4:96.

EXAMPLE 4

25 g of fenvalerate (purity: 98.0%) was dissolved in 50 g of methanol, and 0.12 g of a 28% aqueous ammonia solution and 10 mg of fenvalerate Y crystals were added thereto. The solution was stirred at −6° C. for 8 days.

The weight of fenvalerate Y crystals collected by filtration was 12.6 g (yield 50.4%). The ratio of fenvalerate X to fenvalerate Y was 1:99.

EXAMPLE 5

30 g of fenvalerate (purity: 98.0%) was dissolved in 15 g of methanol, and 0.3 g of triethylamine and 10 mg of fenvalerate Y crystals were added thereto. The solution was stirred at −6° C. for 7 days. To the resulting slurry were added 100 g of 0.2% hydrochloric acid and 40 g of toluene. The aqueous layer was separated and the oily layer was washed with water.

The oily layer was then concentrated under reduced pressure, and 29.7 g of fenvalerate having a fenvalerate X to fenvalerate Y ratio of 19:81 was recovered.

EXAMPLE 6

25 g of fenvalerate (purity: 94.2%) having a fenvalerate X to fenvalerate Y ratio of 54:46 was dissolved in 50 g of methanol, and 0.75 g of triethylamine and 2.5 g of fenvalerate Y crystals were added thereto. The solution was stirred at −17° C. for 2 days.

To this slurry were added 100 g of 1% hydrochloric acid and 100 g of toluene, and the slurry was then separated into aqueous and oily layers. The oily layer was washed with water and concentrated to recover 24.5 g of fenvalerate having a fenvalerate X to fenvalerate Y ratio of 38:62.

EXAMPLE 7

40 g of the fenvalerate used in Example 1 was dissolved in 80 g of methanol. Then, 3.1 g of methanol containing 10.5% of ammonia and 8 g of fenvalerate Y crystals were added thereto. The solution was stirred at −17° C. for 2 days. The weight of fenvalerate Y crystals collected by filtration was 36.4 (yield 71%). The ratio of fenvalerate X to fenvalerate Y was 2.6:97.4.

EXAMPLE 8

40 g of the fenvalerate used in Example 6 was dissolved in 80 g of methanol. Then, 57 mg of sodium hydroxide dissolved in 2 g of methanol and 4 g of fenvalerate Y crystals were added thereto. After stirring at −17° C. for 3 days, 40 g of 5% hydrochloric acid and 40 g of toluene were added and the mixture was stirred at 20° to 25° C. After the aqueous layer was removed, the oily layer was washed twice with water. The toluene was distilled off under reduced pressure and 43.0 g of fenvalerate Y-rich fenvalerate (the ratio of fenvalerate X to fenvalerate Y: 13:87) was obtained.

EXAMPLE 9

40 g of the fenvalerate used in Example 6 was dissolved in 80 g of methanol. 0.36 g of a methanol solution containing 28% of sodium methylate and 4 g of fenvalerate Y crystals were added, and stirred at −17° C. After 3 days, 40 g of 5% hydrochloric acid and 40 g of toluene were added. The mixture was stirred at 20° to 25° C., the aqueous layer was removed, and the toluene layer was washed twice with water. The toluene was removed by distillation. 43.2 g of fenvalerate Y-rich fenvalerate (the ratio of fenvalerate X to fenvalerate Y: 14:86) was obtained.

EXAMPLE 10

40 g of the fenvalerate used in Example 6 was dissolved in 80 g of ethanol. Then, 1.5 g of a methanol solution containing 10.5% of ammonia and 4 g of fenvalerate Y crystals were added thereto. After stirring at −17° C. for 3 days, 40 g of 5% hydrochloric acid and 40 g of toluene were added and the mixture was stirred at 20° to 25° C. After the aqueous layer was removed, the oily layer was washed twice with water. The toluene was distilled off under reduced pressure. 42.7 g of fenvalerate Y-rich fenvalerate was obtained. The ratio of fenvalerate X to fenvalerate Y was 37.9:62.1.

EXAMPLE 11

40 g of the fenvalerate used in Example 6 was dissolved in a mixed solvent of 10 g of toluene and 70 g of n-heptane, and 4 g of fenvalerate Y crystals were added. At −17° C., stirring for 4 days, 40 g of 5% hydrochloric acid was added thereto and then stirred at 30° to 35° C. The aqueous layer was removed and the oily layer was washed with water. The toluene and n-heptane were distilled under reduced pressure, then 43.9 g of fenvalerate Y-rich fenvalerate whose ratio of fenvalerate X to fenvalerate Y was 31:69 was obtained.

EXAMPLE 12

40 g of the fenvalerate used in Example 6 was dissolved in a mixed solvent of 40 g of n-heptane and 32.3 g of methanol. Thereto, 7.7 g of methanol which contained 10.5% of ammonia and 4 g of fenvalerate Y crystals were added. After stirring at −17° C. for 3 days, 40 g of 5% hydrochloric acid and 20 g of toluene were added. The mixture was stirred at 20° to 25° C., the aqueous layer was removed and the oily layer was washed with water. The toluene and n-heptane were distilled off, then 43.3 g of fenvalerate Y-rich fenvalerate which contained fenvalerate X and fenvalerate Y in a weight ratio of 11:89 was obtained.

EXAMPLE 13

40 g of fenvalerate Y-rich fenvalerate, whose purity was 91.3% and the ratio of fenvalerate X to fenvalerate Y was 14.6:85.4, was dissolved in 80 g of methanol. The solution was cooled to 0° C., then 0.3 g of fenvalerate Y crystals were seeded. Under stirring, the mixture was cooled slowly to −15° C. for 3.5 hours, and was then stirred at −15° to −16° C. for 2.5 hours. 28.2 g of the crystals were collected by filtration (yield: 69.8% by weight), whose ratio of fenvalerate X to fenvalerate Y was 3.8:96.2 and whose purity was 98.0%.

EXAMPLE 14

80 g of the fenvalerate Y-rich fenvalerate used in Example 13 was dissolved in 160 g of methanol and 0.1 g of fenvalerate Y crystals were added thereto. After stirring at −18° C. for 18 hours, the solution of 80 g of fenvalerate, whose purity was 92.0% and whose ratio of fenvalerate X to fenvalerate Y was 53.2:46.8, and 153.2 g of methanol was added to the mixture, then 6.2 g of a methanol solution of 10.5% of ammonia was added thereto. After further stirring for 24 hours, about half of the mixture was poured into a mixture of 80 g of toluene and 160 g of 1% hydrochloric acid, the oily layer was washed with water and the toluene was removed by distillation in vacuo. Thus, 82.58 g of the fenvalerate Y-rich fenvalerate was obtained, whose ratio of fenvalerate X to fenvalerate Y was 17.4:82.6.

On the other hand, to the other half of the crystallization mixture, 80 g of fenvalerate, whose ratio of fenvalerate X to fenvalerate Y was 53.2:46.8, dissolved in 160 g of methanol was poured, and 3.1 g of a methanol solution of 10.5% ammonia was added thereto.

After stirring 24 hours, the same procedures were repeated and after an additional 24 hours of stirring the reaction was stopped completely by adding the mixture into 160 g of toluene and 320 g of 1% hydrochloric acid. The second and the third fenvalerate Y-rich fenvalerates were yielded in 81.0 g and 161.5 g, respectively, and their ratios of fenvalerate X to fenvalerate Y were 18.9:81.1 and 18.5:81.5, respectively.

EXAMPLE 15

(A) Preparation of α-cyano-3-phenoxybenzyl 2-(4-difluoromethoxyphenyl)isovalerate (hereinafter "difluoromethoxy ester")

53.1 g of p-methoxyphenylacetonitrile was alkylated with 51.4 g of isopropyl bromide in NaOH/H$_2$O/toluene/Aliquot 336 at reflux for 24 hours. (See, for example, U.S. Pat. Nos. 4,056,509 and 4,144,264.) The crude product was hydrolyzed and demethylated in refluxing concentrated HBr to give α-isopropyl 4-hydroxyphenylacetic acid at 69% overall yeild. The hydroxy acid was alkylated with chlorodifluoromethane in the presence of sodium hydroxide and water according to the procedure set forth at page 2 of British Patent Application No. 2017668A to give crude α-isopropyl-4-difluoromethoxyphenylacetic acid at 62 wt%. 15.9 g of this acid was then reacted with 18.7 g of α-cyano-3-phenoxybenzyl bromide in a mixed solvent of sodium carbonate, water and toluene for 4 hours at 70° C. to give crude difluoromethoxy ester. This ester was purified by chromatography on a silica gel column to yield the final product having an isomer pair ratio of about 50/50.

(B) Preparation of isomers of α-cyano-3-phenoxybenzyl 2-(4-difluoromethoxyphenyl)isovalerate 1. The ester (full racemate) prepared in part (A) above was chromatographed in 8% THF in hexane using recycle on a Waters Prep. L.C. chromatograph to yield the two isomer pairs X and Y.

2. 16.5 g of the α-isopropyl-4-difluoromethoxyphenylacetic acid obtained in part (A) above was resolved into its isomers by reacting it with 8.6 g of (−)-α-methylbenzylamine, and allowing the salt of the l-(−)-amine to crystallize from acetone and hot chloroform diluted with hexane. Recovery of the acid by treatment with hydrochloric acid and extraction gave the (+)- or (S)-acid as a colorless viscous oil. CHCl$_3$[α]$_D^{24°}$=+39.7°. The salt of the d-(+)-amine similarly gave the (−)- or (R)-acid. CHCl$_3$[α]$_D^{24°}$=−38.9°. The (−) and (+) forms of the acid separately were reacted with α-cyano-3-phenoxybenzyl bromide as in part (A) to give (R, S)-α-cyano-3-phenoxybenzyl-(R) (−)-2-(4-difluoromethoxyphenyl)isovalerate and (R,S)-α-cyano-3-phenoxybenzyl (S) (+)-2-(4-difluoromethoxyphenyl)isovalerate, respectively.

Each of these isomer pairs was chromatographed on a Waters Prep. L.C. System 500 on silica gel chromatograph in 8% THF/hexane. The individual Aα, Aβ, Bα and Bβ isomers were thus obtained. Both the Aα and Bβ isomers crystallized to oily solids on standing. Recrystallization of the Aα isomer from methanol at −20° gave a white free flowing solid, m.p. 52°–53.5° C. Recrystallization of the Bβ isomer gave a similar white solid, m.p. 51°–52° C.

EXAMPLE 16

1 g of the ester prepared in part (A) of Example 15 was dissolved in 1.3 g of methanol to which 0.014 part by weight of triethylamine was added. The mixture was chilled to −16° C., and about 1 mg of the Y isomer pair of the ester prepared in part (B)-1 of Example 15 was added. The mixture was allowed to crystallize for 6 days. The resulting slush was acidified with dilute HCl, extracted with ether, dried and stripped. LC examination showed the ratio of the X isomer pair to the Y isomer pair in the resulting crystals to be 28/72.

EXAMPLE 17

0.5 g of the ester prepared in part (A) of Exampel 15 was dissolved in 0.63 g of methanol to which 0.014 part by weight of triethylamine was added. The mixture was chilled to −16° C., and about 1 mg of the Aα isomer of the ester prepared in part (B) of Example 15 was added. The mixture was allowed to crystallize for 13 days. The resulting slush was filtered and the solids were acidified with dilute HCl, extracted with ether, dried and stripped to give 0.264 g of oil. L.C. examination of this recycle of Y isomer showed the ratio of the Aα to Bβ isomers to be essentially 1 to 1.

EXAMPLE 18

A 200 mg sample of difluoromethoxy ester in a 1 ml vial was diluted with 0.25 mg of ethanol, chilled to −15° C. and seeded with a small amount of a ground mixture of solid Aα and Bβ crystals, then stored for 17 hours over night at −16° C. The resulting solids were then broken up and cooling continued for an additional 5 hours. The solids were again broken up and filtered through a prechilled filter, washed with a small amount of methanol and dried by suction to give 36 mg of white solid Y.

EXAMPLE 19

2 g of difluoromethoxy ester was dissolved in 4 g of methanol, and the solution was allowed to cool to −18° C. 50 μl of triethylamine and 2 mg of difluoromethoxy ester Y crystals were added thereto. The solution was stirred for 3 days as it was. To the resulting solution was added 0.2 ml of acetic acid, and filtration was carried out. The crystals thus separated were washed with a small amount of cold methanol (−10° to −20° C.) and dried to obtain 0.72 g of the Y crystals having a melting point of 37° to 38.5° C.

EXAMPLE 20

2 g of difluoromethoxy ester was dissolved in 2 g of methanol and 2 g of n-heptane, and the solution was allowed to cool to −15° C. To the solution were added 2 mg of difluoromethoxy ester Y crystals and 0.33 ml of an 8.4% ammonia/methanol solution, and the mixture was stirred for 4 days. Thereafter, 10 ml of 1% hydrochloric acid and 10 ml of toluene were added thereto. The mixture was stirred, the aqueous layer was removed and the oily layer was washed twice with water. After concentration, 1.92 g of Y-rich difluoromethoxy ester which contained difluoromethoxy ester X and difluoromethoxy ester Y in a weight ratio of 20.7:79.3 and had an $n_D^{21}=1.5436$ was recovered.

EXAMPLE 21

4 g of α-cyano-3-phenoxybenzyl 2-(4-methoxyphenyl)isovalerate (hereinafter referred to as "methoxy ester") was dissolved in 8 g of methanol, and the solution was allowed to cool to −19° C. To the resulting solution were added 4 mg of methoxy ester Aα seed crystals, and 0.24 ml of an 8.4% ammonia/methanol solution, and the mixture was stirred for 3 days. Thereafter, 10 ml of 1% hydrochloric acid and 10 ml of toluene were added thereto. The mixture was stirred, the aqueous layer was removed and the oily layer was washed twice with water. After concentration, 3.96 g of Y-rich methoxy ester which contained methoxy ester X and methoxy ester Y in a weight ratio of 18.1:81.9 and had an $n_D^{22}=1.5652$ was recovered.

EXAMPLE 22

2.02 g of Y-rich methoxy ester prepared in Example 17 was dissolved in 10.1 g of methanol, and the solution was allowed to stand in a refrigerator at −25° C. for one day. Filtration was carried out, and crystals thus separated were washed with a small amount of cold methanol and dried to obtain 1.42 g of methoxy ester Y crystals having a melting point of 50.5° to 54° C.

EXAMPLE 23

2 g of α-cyano-3-phenoxybenzyl 2-(4-ethoxyphenyl)isovalerate (hereinafter referred to as "ethoxy ester") was dissolved in 2 g of methanol and 4 g of n-heptane, and the solution was allowed to cool to −18° C. To the resulting solution were added 2 mg of ethoxy ester Y crystals and 0.12 ml of an 8.4% ammonia/methanol solution, and the mixture was stirred for 3 days. Thereafter, 10 ml of 1% hydrochloric acid and 5 ml of toluene were added thereto, the aqueous layer was removed and the oily layer was washed twice with water. After concentration, 1.96 g of Y-rich ethoxy ester which contained ethoxy ester X and ethoxy ester Y in a weight ratio of 39.0:61.0 and had an $n_D^{22}=1.5582$ was recovered.

EXAMPLE 24

0.6 g of ethoxy ester was dissolved in 3 g of methanol, and the solution was allowed to stand at −25° C. for 7 days. Filtration was carried out to obtain 0.043 g of ethoxy ester Y crystals having a melting point of 43° to 46° C.

Due to the close structural relationship between the compounds of formula (I) or (II), differing only as to the substituent on the phenyl group of the acid moiety, the procedures set forth above in the Examples can be generally used to obtain S phenylisovalerate Y from S phenylisovalerate by crystallization, and to convert S phenylisovalerate to S phenylisovalerate Y in almost quantitative yield by epimerizing X-rich phenylisovalerate mother liquor with a basic catalyst. Thus, methods A, B and C as described above can be used to prepare and obtain the Y isomer pair of each of the compounds of formulas (I) and (II).

Preparation of the insecticidal and acaricidal compositions in accordance with the present invention and the lethal effect thereof will be illustrated with reference to the following Preparation Examples and Test Examples. All parts are by weight.

PREPARATION EXAMPLE 1

0.2 part of fenvalerate Y or fenvalerate Y-rich fenvalerate was dissolved in kerosene to make total weight of 100 parts. Thus, oil sprays of each isomer were obtained. The same procedure can be used for each of the S phenylisovalerate Y and Y-rich S phenylisovalerates obtained in Examples 16 to 24.

PREPARATION EXAMPLE 2

To 20 parts of fenvalerate Y or fenvalerate Y-rich fenvalerate were added 15 parts of Sorpol 3005X (a registered trademark of Toho Kagaku Co.) and 65 parts of xylene. The mixtures were each thoroughly mixed to make a solution. Thus, emulsifiable concentrates of each isomer were obtained.

PREPARATION EXAMPLE 3

To 10 parts of fenvalerate Y or fenvalerate Y-rich fenvalerate were added 20 parts of S-421, 15 parts of Sorpol 3005X (the same as above) and 55 parts of xylene. The mixtures were each thoroughly mixed to make a solution. Thus, emulsifiable concentrates of each isomer were obtained.

PREPARATION EXAMPLE 4

0.1 part of the fenvalerate Y shown in Example 1, 0.2 part of tetramethrin, 7 parts of xylene and 7.7 parts of deodorized kerosene were mixed to make a solution. The solution was filled into an aerosol container. After attaching a valve portion to the container, 85 parts of a propellant (liquefied petroleum gas) was charged therein under pressure through the valve. An aerosol was thus obtained. The same procedure can be used for each of the S phenylisovalerate Y and Y-rich S phenylisovalerates obtained in Examples 16 to 24.

PREPARATION EXAMPLE 5

0.15 g of fenvalerate Y or fenvalerate Y-rich fenvalerate and 0.2 g of d-trans acid isomer of allethrin were dissolved in 20 ml of methanol. The solutions were each uniformly mixed with 99.65 g of a mosquito coil carrier containing tabu-powder, pyrethrum murc and wood powder in a ratio of 3:5:2, and then the methanol was evaporated. To the residue obtained was added 150 ml of water and the mixture was kneaded thoroughly, shaped into a mosquito coil and dried. Thus, mosquito coils of each isomer were obtained.

PREPARATION EXAMPLE 6

0.02 g of fenvalerate Y or fenvalerate Y-rich fenvalerate, 0.05 g of 5-propargylfurfuryl dl-cis, transchrysanthemate and 0.1 g of BHT were dissolved in a suitable amount of chlofororm. The solutions were each absorbed uniformly on filter paper of 3.5 cm × 1.5 cm in size and 0.3 cm in thickness. Thus, fibrous heating fumigant insecticidal and acaricidal compositions for use on a heater were obtained.

PREPARATION EXAMPLE 7

10 parts of fenvalerate Y or fenvalerate Y-rich fenvalerate, 20 parts of Sumithion (the same as above) and 5 parts of Sorpol SM-200 (a registered trademark of Toho Kagaku Co.) were thoroughly mixed. The mixtures were each mixed with 65 parts of 300 mesh diatomaceous earth in a mortar while thoroughly stirring. Thus, wettable powders of each compound were obtained. The same procedure can be used for each of the S phenylisovalerate Y and Y-rich S phenylisovalerates obtained in Examples 16 to 24.

PREPARATION EXAMPLE 8

0.5 part of each of fenvalerate Y or fenvalerate Y-rich fenvalerate was dissolved in 20 parts of acetone, and then 99.5 parts of 300 mesh talc was added thereto. After thoroughly mixing in a mortar while stirring, the acetone was removed by evaporation. Thus, dusts were obtained. The same procedure can be used for each of the S phenylisovalerate Y and Y-rich S phenylisovalerates obtained in Examples 16 to 24.

PREPARATION EXAMPLE 9

3 parts of each of fenvalerate Y or fenvalerate Y-rich fenvalerate, 5 parts of Toyolignin CT (a registered trademark of Toyo Spinning Co.) and 92 parts of GSM Clay (a registered trademark of Zieklite Mining Co.) were thoroughly mixed in a mortar.

Then, the mixtures were each mixed with water of 10% by weight based on the mixture, granulated by means of a granulator and air-dried. Thus, granular preparations were obtained.

PREPARATION EXAMPLE 10

2 parts of each of fenvalerate Y or fenvalerate Y-rich fenvalerate, 2 parts of Cyanox, 5 parts of Toyolignin CT and 91 parts of GSM Clay were thoroughly mixed in a mortar.

Then, the mixture were each mixed with water of 10% by weight based on the mixture, granulated by means of a granulator and air-dried. Thus, fine granular preparations of each compound were obtained.

PREPARATION EXAMPLE 11

0.1 part of fenvalerate Y or fenvalerate Y-rich fenvalerate, 0.2 part of d-trans acid isomer of allethrin, 11.7 parts of deodorized kerosene and 1 part of Atmos 300 (an emulsifier (a registered trademark of Atlas Chemical Co.)) were thoroughly mixed and emulsified by an addition of 50 parts of distilled water. An aerosol container was then filled with the resulting emulsion and 35 parts of a 3:1 mixture of deodorized butane and deodorized propane. A water-base aerosol was thus obtained.

PREPARATION EXAMPLE 12

To 20 parts of each of S phenylisovalerate Y's and Y-rich S phenylisovalerates obtained in Examples 19 to 24 were added 10 parts of Sorpol 3005X (a registered trademark of Toho Kagaku Co.) and 70 parts of xylene. The mixtures were each thoroughly mixed to make a solution. Thus, emulsifiable concentrates of each isomer were obtained.

Similar preparations of the other S phenylisovalerate Y mixtures can be made as indicated above.

The insecticidal and acaricidal activities of the compositions thus obtained were tested as follows.

TEST EXAMPLE 1

Insecticidal activity of fenvalerates on tobacco cut worm (*Spodoptera litura*)

Fenvalerate Y obtained in Example 4, fenvalerate Y-rich fenvalerate obtained in Examples 5 and 6 and common fenvalerate were formulated into a 20% emulsifiable concentrate as usual (Composition: above pesticide 20%; xylene 70%; and Sorpol 3005X (a registered trademark of Toho Kagaku Co.) 10%). These emulsifiable concentrates were each diluted with water to a pre-determined concentration, and mixed with a spreader (Shin-Rino, a registered trademark of Nippon Noyaku Co.) of 3,000 times by weight based on the diluted liquor.

Leaves were cut frm a cabbage plant (prior to the head) cultivated in a flower pot, dipped in the above test solution for 1 minute and air-dried. The dried leaves were placed in a plastic cup (diameter 10 cm, height 4 cm) at a rate of 2 leaves/cup, and the fourth instar larvae of tobacco cut worms were liberated therein. The dead and alive were examined after 24 hours and the values of $LC_{50}$ (concentration required for 50% death) were obtained.

Experiments of three replications were carried out using 10 larvae per group. The results are shown in Table 1.

TABLE 1

| Insecticidal Activity of Fenvalerates on Tobacco Cut Worm | | | |
|---|---|---|---|
| Test Compound Example | Fenvalerate X:Y Ratio | $LC_{50}$ (ppm) | Relative* Efficacy |
| Example 4 | 1:99 | 3.8 | 195 |
| Example 5 | 19:81 | 4.3 | 172 |
| Example 6 | 38:62 | 5.9 | 125 |
| Fenvalerate (common product) | 52:48 | 7.4 | 100 |

*Activity of Fenvalerate (common product) was taken as 100.

TEST EXAMPLE 2

Insecticidal activity of fenvalerates on housefly (*Musca domestica*)

Each pesticide used in Examples 4 and 5 was diluted with acetone to a pre-determined concentration, and 0.5 μl of the solution was applied to the ventral thorax of CSMA-strain housefly female adults by means of a microsyringe. The adults were then liberated in a plastic cup (diameter 11 cm) wherein a bait (3% sugar water) was placed. The dead and alive were examined after 24 hours, and the values of $LD_{50}$ were obtained. The results are shown in Table 2.

TABLE 2

| Insecticidal Activity of Fenvalerates on Housefly | | | |
|---|---|---|---|
| Test Compound Example | Fenvalerate X:Y Ratio | $LD_{50}$ (μg/housefly) | Relative* Efficacy |
| Example 4 | 1:99 | 0.015 | 207 |
| Example 5 | 19:81 | 0.018 | 172 |
| Fenvalerate (common product) | 52:48 | 0.031 | 100 |

*Activity of fenvalerate (common product) was taken as 100.

TEST EXAMPLE 3

The insecticidal activity of fenvalerates on housefly adults (*Musca domestica*) of the aerosols formulated according to the Preparation Examples 4 and 11 was tested by the aerosol test method (Soap and Chemical Specialities, Blue Book, 1965) using a (6 ft)$^3$ Peet Grady's chamber. Thus, with any aerosol, more than 80% of the flies were knocked down within 15 minutes after spraying and more than 70% of the flies were killed by the next day.

TEST EXAMPLE 4

The dusts formulated according to Preparation Example 8 were applied to the potted rice plants 20 days after sowing in a proportion of 2 kg per 10 are by means of a Bell jar duster. Each pot was covered with wire net and about 20 adults of green rice leafhoppers (*Nephotettix cincticeps*) were liberated in the pot. After 24 hours, 100% of the leafhoppers were killed by the dusts.

TEST EXAMPLE 5

Carmine mite female adults (*Tetranychus cinnabarinus*) were made parastic on leaves of the potted kidney bean (primordial leaf-stage) which had grown 9 days since sowing, in a proportion of 10–15/leaf, and bred at 27° C. for a week in a constant temperature room. Then, numerous carmine mites were found to be bred at various growth stages. At this time, a 500 fold aqueous dilute solution of each emulsifiable concentrate formulated according to the Preparation Example 2 was sprayed in a proportion of 10 ml/pot on a turn-table. After 10 days, damage of kidney bean plants by the mites was hardly observed.

TEST EXAMPLE 6

Insecticidal activity of α-cyano-3-phenoxybenzyl 2-(4-difluoromethoxyphenyl)isovalerates on housefly, pea aphid and corn earworm The insecticidal activity of the α-cyano-3-phenoxybenzyl 2-(4-difluoromethoxyphenyl)isovalerate and its isomers was demonstrated according to the following standardized procedures.

A. Housefly: Houseflies (*Musca domestica* Linne) were tested by placing 50 4- to 5-day old houseflies into spray cages and spraying with 0.6 ml of a solution of test compound. After spraying, the flies were anesthetized with $CO_2$ and transferred to a recovery cage containing a milk pad for food. The cages were held for 18–20 hours after which mortality counts were made. Both dead and moribund were counted. The tests were conducted employing several different dosage rates of each test compound.

B. Pea Aphid: Pea aphids (*Acyrthosiphon pisum* Harris) were tested by placing about 100 aphids on broad bean plants. The plants were sprayed with dilutions of acetone solution of test compound into water containing an emulsifier and held in containers under laboratory conditions for 18 to 20 hours at which time the living aphids in the containers were counted. The tests were conducted employing several different dosage rates of each test compound.

C. Corn Earworm: Corn earworm larvae (*Heliothis zea* Boddie) were tested by spraying broad bean plants with dilutions of acetone solution of test compound into water containing an emulsifier. Immediately after spraying, 5 larvae were transferred to each plant and held for 44–46 hours, at which time the dead and moribund larvae were counted. The tests were conducted employing several different dosage rates for each test compound.

TEST RESULTS

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insects or acarine. By assigning the standard pesticide an arbitrary rating of 100, the toxicities of the compounds of the invention were expressed in terms of the toxicity indexes, which compares the toxicity of the compounds of the invention with that of the standard pesticide. That is to say, a test compound having a Toxicity Index of 50 would be half as active, while one having a Toxicity Index of 200 would be twice as active as the standard pesticide.

The results of the above tests are shown in Table 3.

TABLE 3

| | Toxicity Index (Parathion = 100) | | |
|---|---|---|---|
| Compound | Housefly | Pea Aphid | Corn Earworm |
| Common Difluoromethoxy | | | |

TABLE 3-continued

| | Toxicity Index (Parathion = 100) | | |
|---|---|---|---|
| Compound | Housefly | Pea Aphid | Corn Earworm |
| Ester | 219* | 582* | 773* |
| Same, X Isomer Pair | 47* | 45* | 106* |
| Same, Y Isomer Pair | 1100* | 1273* | 1544* |

*High Knockdown

TEST EXAMPLE 7

Insecticidal activity of α-cyano-3-phenoxybenzyl 2-(4-difluoromethoxyphenyl)isovalerates on tobacco cut worm (*Spodoptera litura*)

Emulsifiable concentrates of difluoromethoxy ester Y and Y-rich difluoromethoxy ester formulated according to Preparation Example 12 and a 20% emulsifiable concentrate of common difluoromethoxy ester formulated in the same manner were each diluted with water to a predetermined concentration, and mixed with a spreader (Shin-Rino, a registered trademark of Nippon Noyaku Co.) of 3,000 times by weight based on the diluted liquor.

Leaves were cut from a cabbage plant (prior to the head) cultivated in a flower pot, dipped in the above test solution for 1 minute and air-dried. The dried leaves were placed in a plastic cup (diameter 10 cm, height 4 cm) at a rate of 2 leaves/cup, and the fourth instar larvae of tobacco cut worms were liberated therein. The dead and alive were examined after 24 hours and the values of LC$_{50}$ (concentration required for 50% death) were obtained.

Experiments of three replications were carried out using 10 larvae per group. The results are shown in Table 4.

TABLE 4

Insecticidal Activity of Difluoromethoxy Esters on Tobacco Cut Worm

| Test Compound | Difluoromethoxy Ester X:Y Ratio | LC$_{50}$ (ppm) |
|---|---|---|
| Difluoromethoxy Ester Y | 2:98 | 12 |
| Y-Rich Difluoromethoxy Ester | 20.7:79.3 | 14 |
| Common Difluoromethoxy Ester | 51:49 | 23 |

TEST EXAMPLE 8

Insecticidal activity of S phenylisovalerates (methoxy and ethoxy esters) on housefly (*Musca domestica*)

Each of S phenylisovalerate Y's and Y-rich S phenylisovalerates obtained in Examples 21 to 24 and common racemates was diluted with acetone to a predetermined concentration, and 0.5 μl of the solution was applied to the ventral thorax of CSMA-strain housefly female adults by means of a microsyringe. The adults were then liberated in a plastic cup (diameter 11 cm) wherein a bait (3% sugar water) was placed. The dead and alive were examined after 24 hours, and the values of LD$_{50}$ were obtained. The results are shown in Table 5.

TABLE 5

Insecticidal Activity of S Phenylisovalerates on Housefly

| Test Compound | S Phenylisovalerate X:Y Ratio | LD$_{50}$ (μg/housefly) |
|---|---|---|
| Methoxy Ester Y | 5:95 | 0.17 |
| Y-Rich Methoxy Ester | 18.1:81.9 | 0.20 |
| Common Methoxy Ester (racemate) | 49.5:50.5 | 0.35 |
| Ethoxy Ester Y | 3:97 | 0.28 |
| Y-Rich Ethoxy Ester | 39:61 | 0.46 |
| Common Ethoxy Ester (racemate) | 51:49 | 0.54 |

TEST EXAMPLE 9

Carmine mite female adults (*Tetranychus cinnabarinus*) were made parastic on leaves of the potted kidney bean (primordial leaf-stage) which had grown 9 days since showing, in a proportion of 10–15/leaf, and bred at 27° C. for a week in a constant temperature room. Then, numerous carmine mites were found to be bred at various growth stages. At this time, a 500 fold aqueous dilute solution of each emulsifiable concentrate formulated according to the Preparation Example 12 was sprayed in a proportion of 10 ml/pot on a turntable. After 10 days, damage of kidney bean plants by the mites was hardly observed.

While the invention has been described in detail and with reference to specific embodiments thereof, it will be apparent to one skilled in the art that various changes and modifications can be made therein without departing from the spirit and scope thereof.

What is claimed is:

1. A method for preparing a mixture of isomers of compounds of the formula (I):

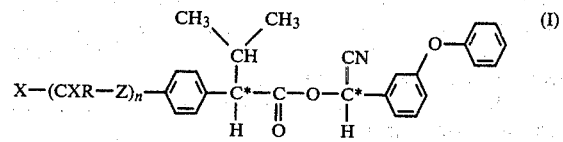

wherein X is hydrogen, Cl or F; R is Cl, F, hydrogen, lower alkyl or lower haloalkyl; Z is oxygen or sulfur; and n is 0 or 1, with the proviso that when n is 0, then X is not hydrogen or Cl, said mixture consisting essentially of the enantiomer pair (S)-α-cyano-3-phenoxybenzyl (S)-2-{4-[X-(CXR-Z)$_n$]phenyl}isovalerate and (R)-α-cyano-3-phenoxybenzyl (R)-2-{4-[X-(CXR-Z)$_n$]phenyl}isovalerate, which method comprises precipitating said mixture as crystals from a solution of α-cyano-3-phenoxybenzyl 2-{4-[X-(CXR-Z)$_n$]phenyl}-isovalerate, and separating the crystals from the mother liquor.

2. The method of claim 1, wherein said α-cyano-3-phenoxybenzyl 2-{4-[X-(CXR-Z)$_n$]phenyl}isovalerate used as a starting material contains more than 60% by weight (S)-α-cyano-3-phenoxybenzyl (S)-2-{4-[X-(CXR-Z)$_n$]phenyl}isovalerate and (R)-α-cyano-3-phenoxybenzyl (R)-2-{4-[X-(CXR-Z)$_n$]phenyl}isovalerate.

3. The method of claim 1, wherein said α-cyano-3-phenoxybenzyl 2-{4-[X-(CXR-Z)$_n$]-phenyl}isovalerate used as a starting material is prepared by precipitating a mixture of (S)-α-cyano-3-phenoxybenzyl (S)-2-{4-[X-(CXR-Z)$_n$]phenyl}isovalerate and (R)-α-cyano-3- phenoxybenzyl (R)-2-{4-[X-(CXR-Z)$_n$]-phenyl}isovalerate as crystals from the solution of α-cyano-3-phenoxybenzyl 2-{4-[X-(CXR-Z)$_n$]phenyl}isovalerate, separating the solution into the crystals and the mother liquor, and bringing α-cyano-3-phenoxybenzyl 2-{4-[(CXR-Z)$_n$]-phenyl}isovalerate in the separated mother liquor into contact with a basic catalyst to induce epimerization thereof.

4. The method of claim 3, wherein said basic catalyst is a base-type ion exchange resin.

5. The method of claim 3, wherein said basic catalyst is removed from the epimerized mother liquor, and the resulting mother liquor is concentrated.

6. A method for preparing a mixture of (S)-α-cyano-3-phenoxybenzyl (S)-2-{4-[X-(CXR-Z)$_n$]-phenyl}isovalerate and (R)-α-cyano-3-phenoxybenzyl (R)-2-{4-[X-(CXR-Z)$_n$]-phenyl}isovalerate wherein X, R, Z and n are as set forth in claim 1 which comprises precipitating the enantiomer pair (S)-α-cyano-3-phenoxybenzyl (S)-2-{4-[X-(CXR-Z)$_n$]-phenyl}isovalerate and (R)-α-cyano-3-phenoxybenzyl (R)-2-{4-[-(CXR-Z)$_n$]-phenyl}-isovalerate as crystals from a solution of α-cyano-3-phenoxybenzyl 2-{4-[X-(CXR-Z)$_n$]-phenyl}isovalerate in the presence of a basic catalyst.

7. A method for preparing α-cyano-3-phenoxybenzyl 2-{4-[X-(CXR-Z)$_n$]-phenyl}isovalerate wherein X, R, Z and n are as set forth in claim 1 which is rich in the enantiomer pair (S)-α-cyano-3-phenoxybenzyl (S)-2-{4-[X-(CXR-Z)$_n$]-phenyl}isovalerate and (R)-α-cyano-3-phenoxybenzyl (R)-2-{4-[X-(CXR-Z)$_n$]-phenyl}isovalerate, which comprises precipitating the enantiomer pair (S)-α-cyano-3-phenoxybenzyl (S)-2-{4-[X-(CXR-Z)$_n$]-phenyl}isovalerate and (R)-α-cyano-3-phenoxybenzyl (R)-2-{4-[X-(CXR-Z)$_n$]-phenyl}isovalerate as crystals from the solution of α-cyano-3-phenoxybenzyl 2-{4-[X-(CXR-Z)$_n$]-phenyl}isovalerate in the presence of a basic catalyst, and recovering the crystals together with α-cyano-3-phenoxybenzyl 2-{4-[X-(CXR-Z)$_n$]-phenyl}isovalerate contained in the mother liquor.

8. The method of claim 6 or 7, wherein said basic catalyst is a nitrogen base.

9. The method of claim 8, wherein said nitrogen base is ammonia or triethylamine.

10. The method of claim 6 or 7, wherein said basic catalyst is selected from the group consisting of alkali metal hydroxides, alkaline earth metal hydroxides, alkali metal oxides, alkaline earth metal oxides, alkali metal amides, alkaline earth metal amides, alkali metal hydrides, alkaline earth metal hydrides, alkali metal alcoholates, and alkaline earth metal alcoholates.

11. The method of claim 10, wherein said basic catalyst is selected from the group consisting of alkali metal hydroxides and alkali metal alcoholates.

12. The method of claim 1, 3, 6 or 7, wherein precipitation of said crystals is carried out by adding seed crystals to the solution.

13. The method of claim 12, wherein the seed crystals are crystals of a mixture of said (S)-α-cyano-3-phenoxybenzyl (S)-2-{4-[X-(CXR-Z)$_n$]-phenyl}isovalerate and (R)-α-cyano-3-phenoxybenzyl (R)-2-{4-[X-(CXR-Z)$_n$]-phenyl}isovalerate.

14. The method of claim 13, wherein said seed crystals are present in an amount greater than 5% based on the α-cyano-3-phenoxybenzyl 2-{4-[X-(CXR-Z)$_n$]-phenyl}isovalerate in said solution.

15. The method of claim 1, 6 or 7, wherein precipitation of said crystals is carried out continuously or semi-continuously.

16. The method of claim 1, 3, 6 or 7, wherein said precipitation is carried out in a lower alcohol or mixed solvent thereof.

17. The method of claim 16, wherein said lower alcohol is methanol.

18. The method of claim 16, wherein a cosolvent is used with the lower alcohol.

19. The method of claim 18, wherein said cosolvent is an aliphatic or alicyclic hydrocarbon.

20. The method of claim 18, wherein said cosolvent is a mixture of an aliphatic or alicyclic hydrocarbon and an aromatic hydrocarbon, whose content is not larger than the aliphatic or alicyclic hydrocarbon.

21. The method of claim 19 or 20, wherein the aliphatic hydrocarbon is pentane, hexane, heptane or octane and the alicyclic hydrocarbon is methylcyclohexane.

22. The method of claim 1, 2, 6 or 7, wherein the compound of the formula (I) is α-cyano-3-phenoxybenzyl 2-(4-methoxyphenyl)isovalerate.

23. The method of claim 1, 2, 6 or 7, wherein the compound of the formula (I) is α-cyano-3-phenoxybenzyl 2-(4-ethoxyphenyl)isovalerate.

24. A method for preparing a mixture of isomers of compounds of the formula (II):

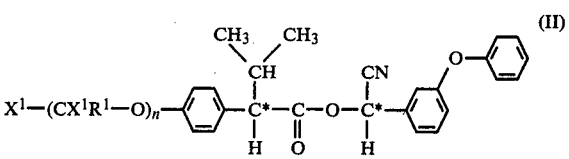

wherein X$^1$ is F; R$^1$ is hydrogen, methyl or methyl substituted with F, and n is 0 or 1, said mixture consisting essentially of the enantiomer pair (S)-α-cyano-3-phenoxybenzyl (S)-2-{4-[X$^1$-(CX$^1$R$^1$-O)$_n$]-phenyl}isovalerate and (R)-α-cyano-3-phenoxybenzyl (R)-2-{4-[X$^1$-(CX$^1$R$^1$-O)$_n$]-phenyl}isovalerate, which method comprises precipitating said mixture as crystals from a solution of α-cyano-3-phenoxybenzyl 2-{4-[X$^1$-(CX$^1$R$^1$-O)$_n$]-phenyl}isovalerate, and separating the crystals from the mother liquor.

25. The method of claim 24, wherein said α-cyano-3-phenoxybenzyl 2-{4-[X$^1$-(CX$^1$R$^1$-O)$_n$]-phenyl}isovalerate used as a starting material contains more than 60% by weight (S)-α-cyano-3-phenoxybenzyl (S)-2-{4-[X$^1$-(CX$^1$R$^1$-O)$_n$]-phenyl}isovalerate and (R)-α-cyano-3-phenoxybenzyl (R)-2-{4-[X$^1$-(CX$^1$R$^1$-O)$_n$]-phenyl}isovalerate.

26. The method of claim 24, wherein said α-cyano-3-phenoxybenzyl 2-{4-[X$^1$-(CX$^1$R$^1$-O)$_n$]-phenyl}isovalerate used as a starting material is prepared by precipitating a mixture of (S)-α-cyano-3-phenoxybenzyl (S)-2-{4-[X$^1$-(CX$^1$R$^1$-O)$_n$]-phenyl}isovalerate and (R)-α-cyano-3-phenoxybenzyl (R)-2-{4-[X$^1$-(CX$^1$R$^1$-O)$_n$-phenyl}isovalerate as crystals from the solution of α-cyano-3-phenoxybenzyl 2{4-[X$^1$-(CX$^1$R$^1$-O)$_n$]-phenyl}isovalerate, separating the solution into the crystals and the mother liquor, and bringing α-cyano-3-phenoxybenzyl 2-{4-[X$^1$-(CX$^1$R$^1$-O)$_n$]-phenyl}isovalerate in the separated mother liquor into contact with a basic catalyst to induce epimerization thereof.

27. The method of claim 26, wherein said basic catalyst is a base-type ion exchange resin.

28. The method of claim 26, wherein said basic catalyst is removed from the epimerized mother liquor, and the resulting mother liquor is concentrated.

29. A method for preparing a mixture of (S)-α-cyano-3-phenoxybenzyl (S)-2-{4-[$X^1$-($CX^1R^1$-O)$_n$]-phenyl}-isovalerate and (R)-α-cyano-3-phenoxybenzyl (R)-2-{4-[$X^1$-($CX^1R^1$-O)$_n$]-phenyl}isovalerate wherein $X^1$, $R^1$, and n are as set forth in claim 24, which comprises precipitating the enantiomer pair (S)-α-cyano-3-phenoxybenzyl (S)-2-{4-[$X^1$-($CXR^1$-O)$_n$]-phenyl}isovalerate and (R)-α-cyano-3-phenoxybenzyl (R)-2-{4-[$X^1$-($CX^2R^1$-O)$_n$]-phenyl}isovalerate as crystals from a solution of α-cyano-3-phenoxybenzyl 2-{4-[$X^1$-($CX^1R^1$-O)$_n$]-phenyl}isovalerate in the presence of a basic catalyst.

30. A method for preparing α-cyano-3-phenoxybenzyl 2-{4-[$X^1$-($CX^1R^1$-O)$_n$]-phenyl}isovalerate wherein $X^1$, $R^1$, O and n are as set forth in claim 24, which is rich in the enantiomer pair (S)-α-cyano-3-phenxybenzyl (S)-2-{4-[$X^1$-($CX^1R^1$-O)$_n$]-phenyl}isovalerate and (R)-α-cyano-3-phenoxybenzyl (R)-2-{4-[$X^1$-($CX^1R^1$-O)$_n$]-phenyl}isovalerate, which comprises precipitating the enantiomer pair (S)-α-cyano-3-phenoxybenzyl (S)-2-{4-[$X^1$-($CX^1R^1$-O)$_n$]-phenyl}isovalerate and (R)-α-cyano-3-phenoxybenzyl (R)-2-{4-[$X^1$-($CX^1R^1$-O)$_n$]-phenyl}isovalerate as crystals from the solution of α-cyano-3-phenoxybenzyl 2-{4-[$X^1$-($CX^1R^1$-O)$_n$]-phenyl}isovalerate in the presence of a basic catalyst, and recovering the crystals together with α-cyano-3-phenoxybenzyl 2-{4-[$X^1$-($CX^1R^1$-O)$_n$]-phenyl}isovalerate contained in the mother liquor.

31. The method of claim 29 or 30, wherein said basic catalyst is a nitrogen base.

32. The method of claim 31, wherein said nitrogen base is ammonia or triethylamine.

33. The method of claim 29 or 30, wherein said basic catalyst is selected from the group consisting of alkali metal hydroxides, alkaline earth metal hydroxides, alkali metal oxides, alkaline earth metal oxides, alkali metal amides, alkaline earth metal amides, alkali metal hydrides, alkaline earth metal hydrides, alkali metal alcoholates, and alkaline earth metal alcoholates.

34. The method of claim 33, wherein said basic catalyst is selected from the group consisting of alkali metal hydroxides and alkali metal alcoholates.

35. The method of claim 24, 26, 29 or 30, wherein precipitation of said crystals is carried out by adding seed crystals to the solution.

36. The method of claim 35, wherein the seed crystals are crystals of a mixture of said (S)-α-cyano-3-phenoxybenzyl (S)-2-{4-[$X^1$-($CX^1R^1$-O)$_n$]-phenyl}isovalerate and (R)-α-cyano-3-phenoxybenzyl (R)-2-{4-[$X^1$-($CX^1R^1$-O)$_n$]-phenyl}isovalerate.

37. The method of claim 36, wherein said seed crystals are present in an amount greater than 5% based on the α-cyano-3-phenoxybenzyl 2-{4-[$X^1$-($CX^1R^1$-O)$_n$]-phenyl}isovalerate in said solution.

38. The method of claim 24, 29 or 30, wherein precipitation of said crystals is carried out continuously or semi-continuously.

39. The method of claim 24, 26, 29 or 30, wherein said precipitation is carried out in a lower alcohol or mixed solvent thereof.

40. The method of claim 39, wherein said lower alcohol is methanol.

41. The method of claim 39, wherein a cosolvent is used with the lower alcohol.

42. The method of claim 41, wherein said cosolvent is an aliphatic or alicyclic hydrocarbon.

43. The method of claim 41, wherein said cosolvent is a mixture of an aliphatic or alicyclic hydrocarbon and an aromatic hydrocarbon, whose content is not larger than the aliphatic or alicyclic hydrocarbon.

44. The method of claim 42 or 43, wherein the aliphatic hydrocarbon is pentane, hexane, heptane or octane, and the alicyclic hydrocarbon is methylcyclohexane.

45. The method of claim 24, 25, 29 or 30, wherein the compound of the formula (II) is α-cyano-3-phenoxybenzyl 2-(4-difluoromethoxyphenyl)isovalerate.

46. The method of claim 1, 6, 7, 24, 29 or 30, wherein n is 1.

* * * * *